United States Patent [19]

Tischer et al.

[11] Patent Number: 5,480,790
[45] Date of Patent: Jan. 2, 1996

[54] WATER-SOLUBLE PROTEINS MODIFIED BY SACCHARIDES

[75] Inventors: Wilhelm Tischer, Peissenberg; Joachim Klein, Braunschweig; Rolf-Joachim Müller, Gifhorn; Stephan Engelke, Drensteinfurt, all of Germany

[73] Assignees: Boehringer Mannheim GmbH, Mannheim-Waldhof; Gesellschaft fur Biotechnologische Forschung mbH, Braunschweig, both of Germany

[21] Appl. No.: 680,334

[22] Filed: Apr. 4, 1991

[30] Foreign Application Priority Data

Apr. 5, 1990 [DE] Germany .......................... 40 11 084.2

[51] Int. Cl.⁶ .............................. C07K 1/113; C12N 9/96
[52] U.S. Cl. ..................... 435/188; 436/86; 530/405; 530/406; 530/409; 530/410; 530/411
[58] Field of Search ...................... 530/395, 402, 530/410, 411, 406, 405, 409; 435/188, 177, 183, 195, 200, 208, 215; 436/86, 87

[56] References Cited

U.S. PATENT DOCUMENTS

| | | | |
|---|---|---|---|
| 4,460,683 | 7/1984 | Gloger et al. | 435/177 |
| 4,931,392 | 6/1990 | Rehmer et al. | 435/188 |
| 4,950,609 | 8/1990 | Tischer et al. | 435/18 |
| 5,043,436 | 8/1991 | Ogawa | 435/203 |
| 5,068,183 | 11/1991 | Ogawa | 435/203 |

FOREIGN PATENT DOCUMENTS

| | | |
|---|---|---|
| 0222380 | 11/1956 | European Pat. Off. |
| 63-219787 | 9/1988 | Japan . |
| 64-45391 | 2/1989 | Japan . |
| 2219571 | 9/1990 | Japan . |

OTHER PUBLICATIONS

Kagotani et al., Chem./Abs. vol. 113 (25) entry #227,144a (1990).
Nahayama et al., Chem. Abs. vol. 114 (17) entry #159878m (1991).
Christensen et al., Process Biochem, pp. 25–26 Jul./Aug. 1976.
Vorberg et al., J. Immunol. Meta., vol. 132 pp. 81–89, (1990).
Chernyale et al., Chem. Abs. vol. 113 (23) entry 209415k (1990).
Klein, J. (1986) Makromol. Chem. Rapid Commun. 7:621–625.
Klein, J. (1988) Makromol. Chem. 189:805–813.
Klein, J. (1987) Makromol. Chem. 188:1217–1232.
Kohn, J., et al. (1984) Review—Kohn and Wilchek. Humana Press.
R. D. Schmid, (1979) Adv. Biochem. Engl. 12:41–118.
Klein, J., (1990) Makromol. Chem., Rapid Commun. 11:477–483.
Klein, J., (1989) Makromol. Chem., 190:2527–2534.
Klein, J., (1989) Makromol. Chem., Rapid Commun. 10:629–636.
Klein, J., (1985) Makromol. Chem., Rapid Commun. 6:675–678.
Stephan Engelke (1989) Thesis.
Chemical Abstracts, vol. 108, Nr. 21, May 23, 1988, A. Matsushima et al. "Synthetic Macromolecule–Modified Enzymes", p. 310 No. 182 535g.
Chemical Abstracts, vol. 104, No. 2, Jan. 13, 1986, No. 6 251v "Poly(vinylsaccharide)s, 1. Emulsion Polymerization of Poly(methacryloylglucose)", p. 6259.
Chemical Abstracts, vol. 107, No. 8, Aug. 24, 1987, J. Klein et al., "Poly(vinylsaccharides). 2. Synthesis of Some Poly-(vinylsaccharides) of the Amide Type and Investigation of Their Solution Properties", p. 59563 No. 59 558u.
Chemical Abstracts, vol. 112, No. 10, Mar. 5, 1990, J. Klein et al. "Poly(vinylsaccharides). 6. Synthesis and Characterization of New Poly(vinylsaccharides) of the Urea Type", p. 78074, No. 78 064z.
Chemical Abstracts, vol. 112, No. 12, Mar. 19, 1990, J. Klein et al., "Poly(vinylsaccharides). 5. Synthesis and Characterization of Poly(vinylsaccharides) of the Amides Type with Disaccharides in the Side Chain", p. 99342, No. 99 337f.
Chemical Abstracts, vol. 113, No. 2, Jul. 9, 1990, J. Klein et al., "Poly(vinylsaccharides). 7. New Surfactant Polymers based on Carbohydrates", p. 8443, No. 8 431p.

Chemical Abstracts, vol. 114, No. 4, Jan. 28, 1991, J. Klein et al., "Poly(vinylsaccharides). 8. New Anionic Poly(vinylsaccharides)", p. 24687, No. 24 677z.

*Primary Examiner*—Jeffrey E. Russel
*Attorney, Agent, or Firm*—Felfe & Lynch

[57] ABSTRACT

A water-soluble protein conjugate modified by saccharides is covalently bound to a carbohydrate backbone via a saccharide group. Such protein conjugates modified by saccharides can be produced in a simple way by polymerizing a vinylsaccharide and conjugating in a known way the poly(vinylsaccharide) obtained in this way with the protein, which is preferably an enzyme. The protein conjugates according to the present invention are stable over long time periods at a high enzymatic activity and also in aqueous solution and are thus particularly suitable for use in test kits.

27 Claims, 3 Drawing Sheets

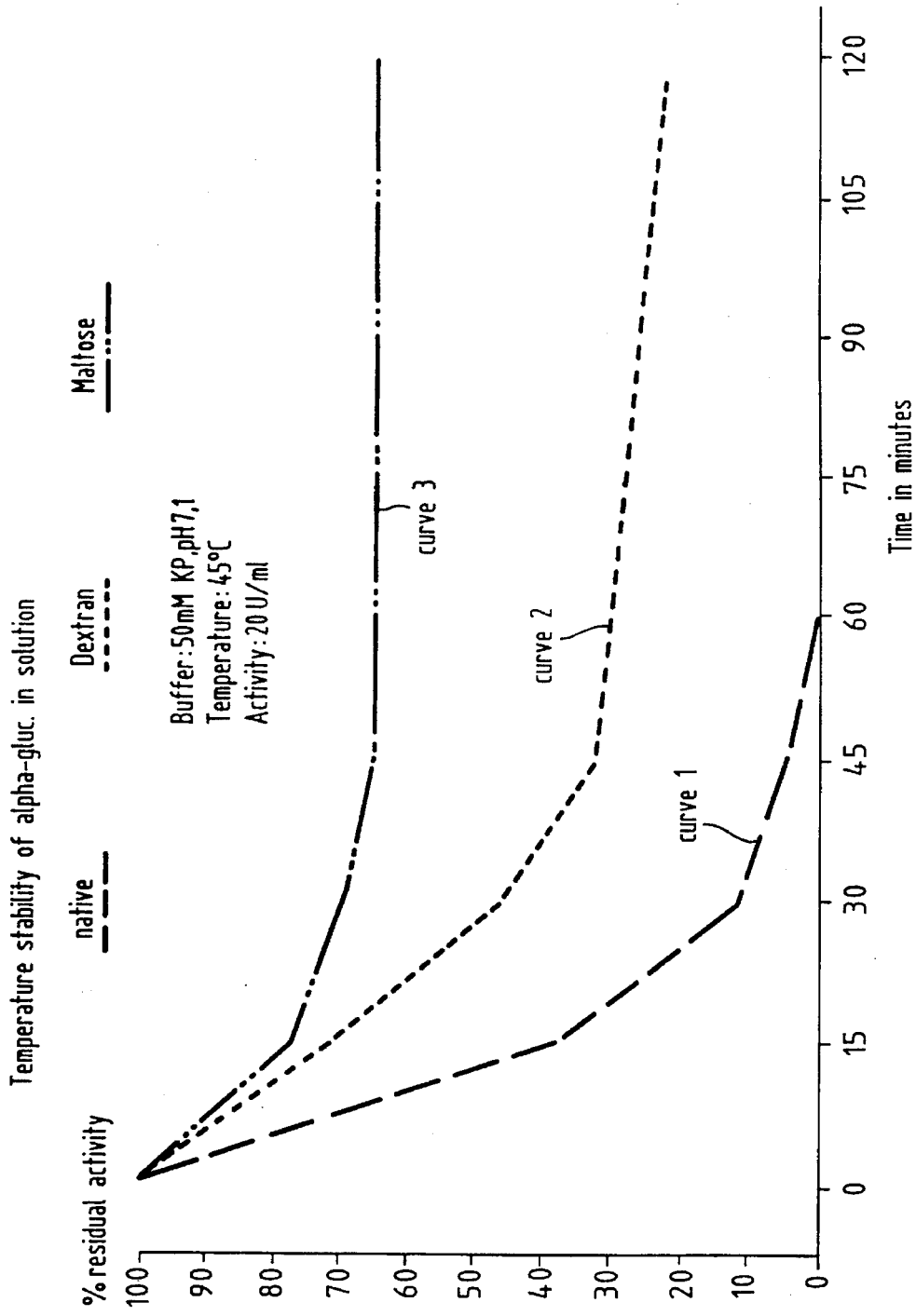

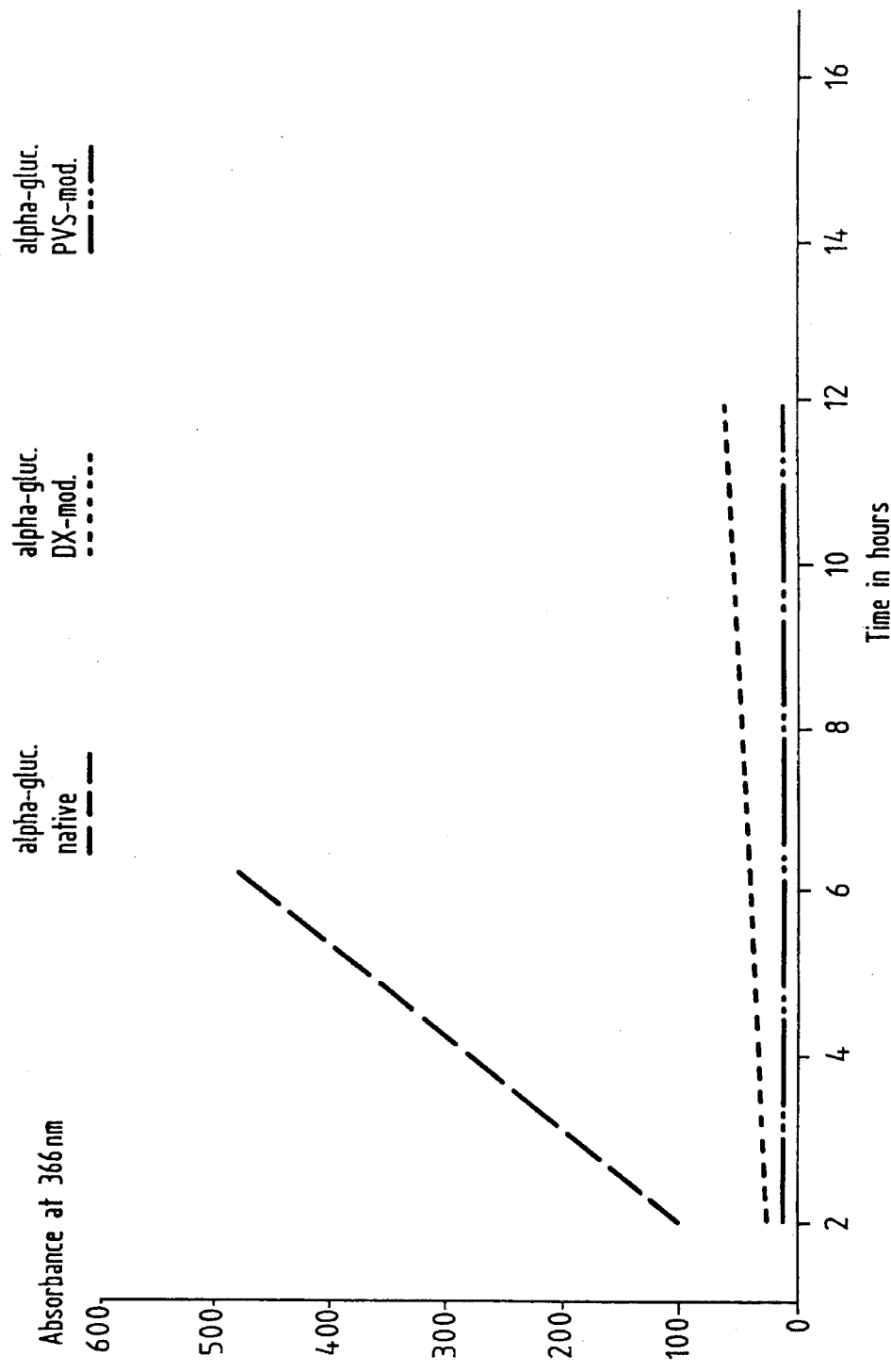

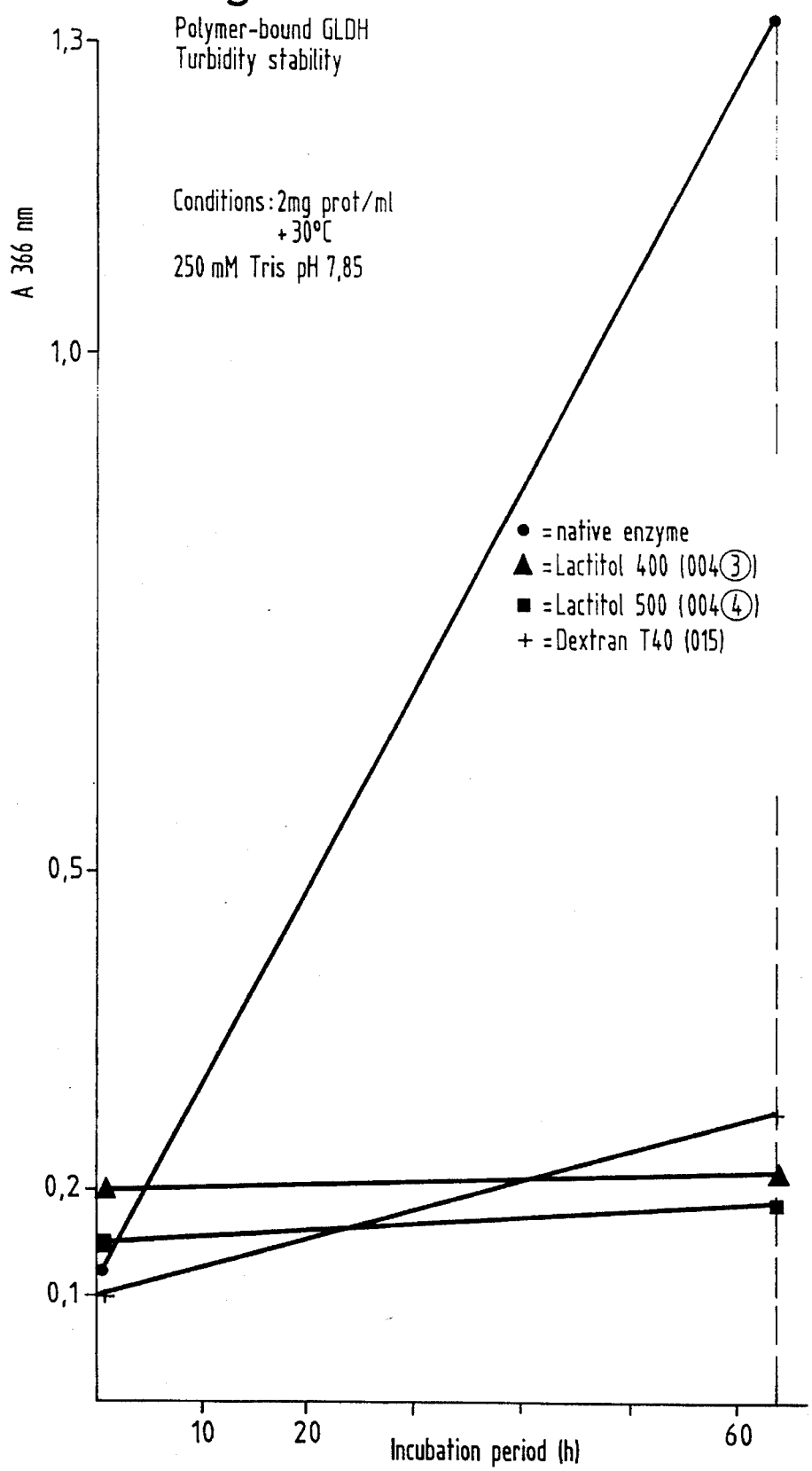

WATER-SOLUBLE PROTEINS MODIFIED BY SACCHARIDES

DESCRIPTION

The invention concerns water-soluble proteins modified by saccharides, a process for their production as well as their use.

It is known that proteins can be modified in order to improve certain properties such as their solubility, their compatibility when using hydrophobic materials such as e.g. plastics, their storage stability, their activity in non-aqueous systems e.g. in organic solvents, or their biological half-times.

It is known from R. D. Schmidt, Adv. Biochem. Eng. (1979) 12, 41–118 that e.g. the stability, solubility or enzymatic activity of proteins can be modified by a chemical derivatization with low molecular or also with high molecular reagents as well as via a cross-linking with bi- or polyfunctional reagents.

Water-soluble polysaccharides such as dextran or Ficoll have previously proven to be particularly suitable reagents. Thus, it is known e.g. from DE-OS 35 41 186 that a water-soluble peroxidase can be produced in this manner. Furthermore a process for stabilizing creatine kinase is known from EP-A-0 222 308, the stabilization of sarcosine oxidase is known from EP-A-0 201 805 and a process for producing a soluble liver uricase is known from EP-A-0 069 379. In all these described processes the proteins are bound covalently to a water-soluble carrier substance which is usually a polysaccharide.

Polysaccharides are, however, readily degraded by glycohydrolases. This is a disadvantage when the proteins (enzymes) modified by polysaccharides are intended to be used for enzymatic analysis in clinical chemistry since the sample material used in this case contains such endogenous glycohydrolases. In addition polysaccharides can be cleaved by periodate (a reagent which is often used in clinical chemistry for colorimetric test reactions). Polysaccharides such as soluble starches and celluloses often have few functional groups for binding the proteins which is a result of their branching or their derivatization, which must for example be carried out in order to improve or to achieve solubility in water.

The object of the present invention is therefore to provide protein conjugates which do not have the disadvantages described above.

This object is achieved by covalently binding the protein to a poly(vinylsaccharide) via a saccharide residue.

Surprisingly it turned out that the stability and activity of proteins dissolved in an aqueous solution can be improved by conjugating the protein with a saccharide residue which in turn is covalently linked to a vinyl residue of a polyvinyl chain as a backbone. This covalent bond is usually formed via an ether, ester or amido group.

The production of such poly(vinylsaccharides) is known and is comprehensively described by J. Klein et al. in Macromol. Chem. 188, 1217–1232 (1987); Macromol. Chem. Rapid Commun. 7, 621–625 (1986); and in Macromol. Chem. 189, 805–813 (1988) as well as in the Thesis of S. Engelke, TU Braunschweig FRG (1989) which are herewith explicitly incorporated by reference and hereby made part of the application. Poly(vinylsaccharides) are water-soluble polymers which are obtained by means of a vinyl polymerization from vinylsaccharide monomers which are in turn usually produced by a coupling reaction of an unsaturated vinyl component with a carbohydrate derivative. The polymerization can either take place cationically or by a radical path. Catalyzers for the radical polymerization are e.g. peroxide, and $BF_3$ is for example used as a catalyzer for the cationic polymerization.

The Klein 1987 paper reports:

Poly(vinylsaccharide)s belong to a type of water soluble polymer, which are prepared by a vinyl type polymerization of well defined and characterized saccharide based monomers. These monomers result from a coupling reaction of an unsaturated component with a carbohydrate derivative, and the linkage is usually formed by an ether-, ester- or amido group.

Scheme 1
[J. Klein Makromol. Chem. Rapid Commun. 6:675 (1985)]

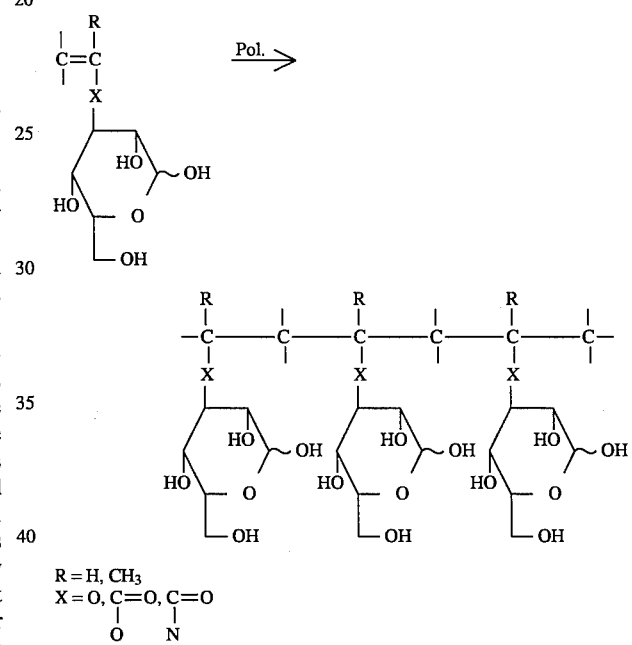

Scheme 1. Synthesis of poly(vinylsaccharide)s

To obtain linear polymers from vinyl compounds containing carbohydrate moieties it is necessary to make sure during the synthesis of the monomer that only the monovinyl derivative of the carbohydrate is prepared and isolated.

For the preparation of an unsaturated monofunctional ester or ether of a carbohydrate all the hydroxyl groups but one must be protected by use of dissopropylidene or acetyl protecting groups. These monomers were polymerized mostly in the organosoluble protected form and were brought into the water soluble one by acidic or alkaline hydrolysis.

Another way to monovinylized saccharides is the synthesis of unsaturated amides from amino-sugars (Whistler, R. L. et al. J. Org. Chem. (1961) 26:1583) or sugar-lactones (Kobayashi, K., et al. Polymer J. (1983) 15:667).

Poly(vinylsaccharide)s must structurally be seen as a connecting link between the total synthetic water soluble polymers A and the naturally occurring biopolymers D as shown in Scheme 2.

Scheme 2. Different types of water soluble polymers.

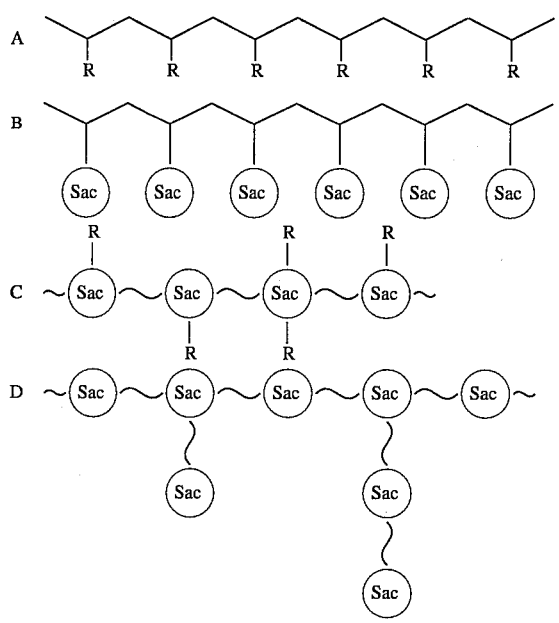

R = synthetic residues, for example: $CH_3$, alkyl, acryl;
Sac = saccharide residues, for example: glucose, mannose, galactose.
A: Total synthetic polymers (petrochemical basis);
B: Poly(vinylsaccharide)s (petrochemical and biomass basis);
C: Modified biopolymers (biomass and petrochemical basis);
D: Natural biopolymers (biomass basis)

Poly(vinylsaccharide)s B have synthetic backbone and side chains derived from naturally occurring carbohydrates, while the modified biopolymers C are built up from a carbohydrate backbone and synthetic side chains. This type C is represented for example by methylcelluloses, hydroxyethylcelluloses, or modified starch and guar gum.

In connection with the synthesis of type B polymers the contribution of Pfannemüller et al. (W. N. Emmerling and B. Pfannemüller Makromol Chem. (1983) 184:1441) have to be mentioned. In comparison to our approach this reflects the situation that in general two synthetic routes exist to obtain functionalized linear or crosslinked vinyl polymers: (1) the preparation of a precursor polymer with subsequent functionalization by polymer analogous reaction (Emmerling ibid), (2) the preparation of the properly functionalized monomer with subsequent polymerization (J. Klein, et al., Makromol. Chem., Rapid Commun. 6:675 (1985); T. P. Bird, et al., Chem. Ind. (London) 1960, 1331; M. Imoto and S. Kimura, Makromol. Chem. 53:219 (1962); S. Kimura and K. Hirai, Makromol. Chem. 58:232 (1962); S. Kimura and M. Imoto, Makromol. Chem. 50:155 (1961).

Since polymer analogous reactions are usually incomplete and pose considerable difficulties for an exact compositional analysis, route (2) should be followed if well defined polymers are required as in the process of establishing structure-property relations.

For the study of the solution properties of different polyvinylsaccharides, we looked for monomer that might show good solvation behavior in aqueous systems.

N-Substituted (meth)acrylamides should meet these requirements, and also their synthesis did not need use of protecting groups.

Use of commercially available amino-sugars, such as glucosamine hydrocholored, was possible, and via the reductive amination of reducing sugars to the 1-amino-1-deoxy-sugars further interesting components could be prepared. Coupling of the amino-sugars with the reactive (meth)acrylic component was carried out at low temperatures in an alkaline aqueous system or in methanol to guarantee that only the amide was prepared and the sugar esters that might be formed in a side reaction will be destroyed immediately. The yields were satisfactory and the main difficulty was the purification of the monomers by crystallization which did not succeed in the case of the 1-deoxy-1-methacrylamidomaltitol (T. P. Bird ibid). Scheme 3 shows the monomers we used for our investigation.

Scheme 3. Prepared vinylsaccharide monomers.

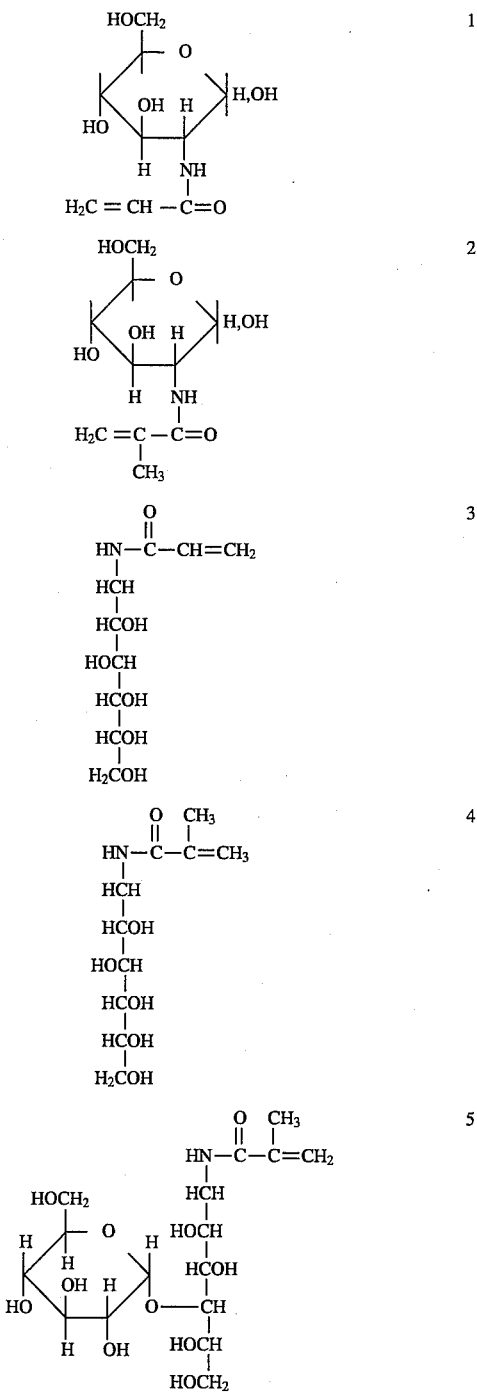

Scheme 3. Prepared vinylsaccharide monomers.

2-Acrylamido-2-deoxy-D-glucose (1),
2-deoxy-2-methacrylamido-D-glucose (2),
1-acrylamido-1-deoxy-D-glucitol (3),
1-deoxy-1-methacrylamido-D-glucitol (4),
and
1-deoxy-1-methacrylamidomaltitol (5)

The highest molecular weights were prepared by polymerization at low temperatures using the redox initiator system $(NH_4)_2S_2O_5$. Reactions at higher temperature (t>40° C.) which were initiated with $H_2O_2$ resp. the water soluble azoinitiator 2,2'-dimethyl-2,2'-azodipropanamidine hydrochloride, gave lower degrees of polymerization ($P_w$). The various polymerizations had different inhibition times in the beginning of the polyreaction, so that the reaction times and yields cannot be compared. The vinylsaccharide monomers followed the common rules of free radical polymerization. As the crystallization of 5 failed, we used the product as a syrup with small impurities, that could be seen by $^{13}CNMR$, for the polymerization reaction. In this way, much smaller degrees of polymerization than for the monomers resulted.

The poly(vinylsaccharide)s were soluble in water and dimethyl sulfoxide but insoluble in common organic solvents as methanol, pyridine, dichloromethane, and toluene.

2-Acrylamido-2-deoxy-D-glucose (1): Glucosamine hydrochloride (0.1 mol; 21.56 g) and sodium nitrite (0.2 g) as inhibitor were dissolved under nitrogen atmosphere in 100 ml of a 0.3 M potassium carbonate solution, and the mixture was cooled to 0° C. Under vigorous stirring, acryloyl chloride (0.2 mol; 18.1 g) was added while the temperature was kept below 5° C. Stirring was continued for 3 h at 0°–5° C. and further 2 h while the mixture was allowed to come to room temperature. Finally, it was left at room temperature for 14 h. The solution was poured into 1 l of dry ethanol and strongly mixed. The resulting suspension was filtered by suction, and the cake was washed three times with 250 ml of 95% ethanol. To the combined filtrates and washings 1 l of ether was added and the solution was kept at 0° C. for 24 h. The desired product crystallized as white cubes, while the yellowish needles that might appear were a by-product. It could be separated by stirring up the whole mixture and decanting the liquid with the floating needles while the product remained on the ground of the reaction flask. By addition of 1 l of ether to the mother liquid a second crop could be isolated. The product was recrystallized two times from water/ethanol/ether. Yield 8.1–10.5 g (35–45%), m.p.:124°–125° C.

$^{13}C$ NMR ($D_2O$, TMS)($\alpha$ and $\beta$ anomer): $\delta$=55.08 ($C^2\alpha$); 56.73 ($C^2\beta$); 60.56 ($C^0\alpha$); 60.68 ($C^6$); 69.74, 70.03, 70.58, 71.44. ($C^3\alpha+\beta$, $C^4\alpha+\beta$); 73.74 ($C^5\alpha$); 75.78 ($C^5\beta$); 90.7 ($C^1\alpha$); 94.79 ($C^1\beta$); 127.65, 127.83 (=$CH_2$, $\alpha+\beta$); 129.52, 129.80 (—CH=, $\alpha+\beta$); 168.32, 168.71 (C=O, $\alpha+\beta$).

$C_9H_{15}NO_6$ (233.2) Calc. C 46.35; H 6.48; N 6.00. Found C 46.28; H 6.52; N 5.71.

2-Deoxy-2-methacrylamido-D-glucose (2): Glucosamine hydrochloride ( 0.06 mol; 13.25 g), sodium carbonate (0.2 mol; 21.2 g) and sodium nitrite (0.2 g) were dissolved under nitrogen atmosphere at 0° C. in 100 ml of $H_2O$. Methacryloyl chloride (0.12 mol; 13.0 g) was added under vigorous stirring. The reaction was carried out similar to the synthesis of 1 and gave the product as a white powder after two recrystallizations from water/ethanol/ether. Yield: 8.3–8.9 g (56–60%), p.m. (decomp.): 198°–199° C.

$^{13}C$ NMR ($D_2O$, TMS) ($\alpha+\beta$ anomer): $\delta$=18.46, 18.54 (—$CH_3\alpha+\beta$); 54.89 ($C^2\alpha$); 57.53 ($C^2\beta$); 61.41, 61.51 ($C^6\alpha+\beta$); 70.75, 71.26, 71.67, 72.23 ($C^3\alpha+\beta$, $C^4\alpha+\beta$); 74.28 ($C^5\beta$); 76.47 ($C^5\alpha$); 91.50 ($C^1\beta$); 95.46 ($C^1\alpha$); 121.89, 122.06 (=$CH_2\alpha+\beta$); 139.63, 139.89

$$(-\underset{|}{C}=\alpha+\beta);$$

172.69, 173.07 (C=O$\alpha+\beta$). $C_{10}H_{17}NO_6$(247.3)

Calc. C 48.58; H 6.93; N 5.67. Found C 48.42; H 6.98; N 5.43.

1-Amino-1-deoxy-D-glucitol: Glucose (0.55 mol; 100 g) was dissolved in 500 ml of $H_2O$, and 40 ml of an 80% hydrazinium hydrate solution (1 mol) were added. The mixture was stirred slowly for 14 h and filled into a high pressure autoclave. Freshly activated Raney nickel (20 g) was added and the mixture was hydrogenated for 3 h at 50° C. while stirring with about 1000 r.p.m. The autoclave was depressurized and the product-catalyst mixture was filtered. The blue filtrate was treated with diacetyldioxime (2,3-butanedionedioxime) to remove the dissolved nickel. The product was concentrated to a clear yellowish syrup and was crystallized in the refrigerator. The white crystals were filtered off and washed with MeOH. If necessary the product was purified using the oxalate method of J. W. Long, G. N. Bollenbach in "Methods of Carbohydrate Chemistry" ed. by R. L. Whistler and M. L. Wolfrom, Academic Press N.Y. 1963, Vol. 2, P. 79). Yield: 80 g (80%), m.p.: 127° C.

$^{13}C$ NMR ($D_2O$. TMS): $\delta$=43.36 ($C^1$); 63.39 ($C^6$); 71.14, 71.62, 74.06 ($C^2$–$C^5$).

$C_6H_{15}NO_5$ (181.2) Calc. C 39.77; H 8.34; N 7.73. Found C 39.98; H 8.12; N 7.72.

1-Acrylamido-1-deoxy-D-glucitol (3): 1-Amino-1-deoxy-D-glucitol (0.16 mol; 29 g) and 0.2 g $NaNO_2$ were dissolved under a nitrogen atmosphere at 0° C. in 100 ml of a 0.3M $K_2CO_3$ solution. Acryloyl chloride (0.32 mol; 28.96 g) was added under vigorous stirring. The reaction was carried out similar to the synthesis of 1. After addition of ether, white crystals and a yellow oil were formed. The crystals were separated and gave the product, while the oil was discharged. Stepwise addition of 2 l of ether to the mother liquid and storing it in the refrigerator gave more of the desired product. For further purification the crystals were recrystallized twice from water/ethanol/ether. Yield: 22.2 g (59%), m.p.: 125° C.

$^{13}C$ NMR ($D_2O$, TMS): $\delta$=42.32 ($C^1$); 63.10 ($C^6$); 70.59, 71.35, 71.44, 71.73 ($C^2$–$C^5$); 127.78 (=$CH_2$); 130.24 (—CH=); 168.98 (C=O).

$C_9H_{17}NO_6$ (235.2) Calc. C 45.95; H 7.28; N 5.95. Found C 45.72; H 7.28; N 5.81.

1-Deoxy-1-methacrylamido-D-glucitol (4): This was prepared similar to method A given by Whistler et al. (J. Org. Chem. 26:1583 (1961). The product was recrystallized two times from water/ethanol/ether. Yield: 68–70%, m.p.: 160°–161° C. $^{13}C$ NMR ($D_2O$, TMS): $\delta$=18.06 (—$CH_3$); 42.55 ($C^1$); 63.14 ($C^6$); 70.61, 71.38, 71.50, 71.91 ($C^2$–$C^5$); 121.54 (=$CH_2$); 139.34 (—C=); 172.23 (C=O).

$C_{10}H_{19}NO_6$ (294.3) Calc. C 48.19; H 7.68; N 5.62. Found C 48.37; H 7.73; N 5.60.

1-Amino-1-deoxymaltitol: It was prepared according to the prescription of Lemieux [U.S. Pat. No. 2,830,983 (1958) Chem. Abstr. 52 14668 (1958)]. Commercial maltose (0.438 mol; 150 g) was dissolved in 500 ml of water and stirred with 40 ml of an 80% hydrazinium hydrate (1 mol) solution for 14 h. The mixture was filled into a high pressure autoclave, 20 g of freshly prepared Raney nickel was added, and it was hydrogenated for 4.5 h at 50° C. under stirring with about 1000 r.p.m. The autoclave was depressurized and the catalyst filtered off. The blue filtrate was treated with diacetyldioxime to remove the pressure at low temperature to a viscous syrup, which was covered with dry MeOH. While standing at room temperature for a week, the product crystallized as a white solid mass, which was separated from a small amount of yellowish syrup by filtration and washing with MeOH. Yield: 113 g (75%), m.p.: 143°–145° C.

$^{13}$C NMR (D$_2$O, TMS); δ=43.39 (C$^1$); 61.75 (C$^6$); 63.56 (C$^6$); 69.75, 73.15 (C$^2$, C$^3$, C$^5$); 70.73 (C$^4$'); 72.95 (C$^5$'); 73.84 (C$^2$'); 74.22 (C$^3$'); 83.25 (C$^4$); 101.87 (C$^1$').

C$_{12}$H$_{25}$NO$_{10}$ (343.3) Calc. C 41.98; H 7.34; N 4.08. Found C 41.55; H 7.15; N 3.71.

1-Deoxy-1-methacrylamidomaltitol (5): 1-Amino-1-deoxymaltitol (25.75 g; 0.075 mol) was pulverized under dry nitrogen atmosphere and suspended at −10° C. in 150 ml of MeOH. To this suspension methacrylic anhydride (11.56 g; 0.075 mol) was slowly added and the temperature elevated to 0° C. The mixture was held at this temperature for 24 h and at 15° C. for further 4 h. The reaction was stopped, the solution filtered off from a rest of unreacted 1-amino-1-deoxymaltitol and the filtrate concentrated under reduced pressure to a slightly yellowish syrup. It was dissolved in 50 ml of water and the solution extracted five times with 50 ml of ether After concentrating i.vac. a clear, nearly colourless syrup resulted, which should a neutral reaction in water and which could not be crystallized. Yield: 27.77 g (90%).

$^{13}$C NMR (D$_2$O, TMS): δ=18.16 (–CH$_3$); 42.98 (C$^1$); 60.87 (C$^6$'); 62.62 (C$^6$); 69.92 (C$^4$'); 70.71 (C$^2$); 71.51 (C$^3$); 72.15 (C$^2$'); 73.01 (C$^5$, C$^5$'); 73.43 (C$^3$'); 82.29 (C$^4$); 100.94 (C$^1$'); 121.71 (=CH$_2$); 139.44

172.5 (C=O).

C$_{16}$H$_{29}$NO$_{11}$ (411.4) Calc. C 46.75; H 7.10; N 3.40. Found C 46.10; H 7.48; N 3.33.

Hydrogenation of poly(2-deoxy-2-methacrylamido-D-glucose): Sample No. 6 (0.550 g) was dissolved in 50 ml of H$_2$O and treated with a twentyfive-fold excess of NaBH$_4$ (2.104 g). The hydride was added at room temperature in small portions. After 2 h the mixture was neutralized with dilute HCl to a pH of 7. The resulting solution showed a slight turbidity and was dialysed for several days against distilled H$_2$O in a dialysis tube (Thomapor, FRG) to remove salts and boric acid. The clear and colourless solution was filtered from dust and freeze dried. Yield: 0.547 g (99%).

Synthesis of polymers: The polymerizations were carried out in aqueous solution. As initiator systems we used H$_2$O$_2$, 2,2'-dimethyl-2,2'-azodipropanamidine hydrochloride (WAKO-Chemie, Düsseldorf, FRG), and the redox couple (NH$_4$)$_2$S$_2$O$_8$/Na$_2$S$_2$O$_5$. The monomers were dissolved in doubly distilled, degassed water in reaction flasks held under a highly purified nitrogen atmosphere. We used different round-bottomed glass flasks with double walls so that they could be accurately thermostated. Each flask was supplied with a nitrogen in- and outlet, a septum and a stirrer (magnetic and, if necessary, a blade stirrer). The reaction was started by injecting the initiator, dissolved in a small amount of water, through the septum. To stop the polymerization, the mixture was poured into a large amount of dust-free MeOH. The polymers were separated as snow-white flakes. To improve the precipitation, especially in the case of the lower molecular weight polymers, addition of 1% sodium acetate to the MeOH was useful. The polymers were taken up in water and precipitated for a second time in MeOH to remove possibly included monomers and at last dissolved in water and freeze dried. The details of the polymerizations are listed in Table 5.

TABLE 5

Details of the preparation or poly(vinylsaccharide)s by solution polymerization in water

| Sample No. | Monomer type | Monomer conc. in mol/l | Oxi. conc.[a] in mol/l | Red. conc.[b] in mol/l | Reaction temp. in °C. | Reaction time in h | Yield in % |
|---|---|---|---|---|---|---|---|
| 1 | 1 | 0.43 | $1.0 \cdot 10^{-2}$ | $6.4 \cdot 10^{-3}$ | 25 | 15 | 98 |
| 2 | 1 | 0.07 | $2.8 \cdot 10^{-3}$ | $1.8 \cdot 10^{-3}$ | 4 | 10 | 12 |
| 3 | 1 | 0.15 | $2.8 \cdot 10^{-3}$ | $1.8 \cdot 10^{-3}$ | 4 | 10 | 72 |
| 4 | 1 | 0.43 | $7.8 \cdot 10^{-3}$ | $5.0 \cdot 10^{-3}$ | 2 | 1 | 40 |
| 5 | 2 | 0.26 | $1.0 \cdot 10^{-4}$ | $7.2 \cdot 10^{-5}$ | 4 | 12 | 18 |
| 6 | 2 | 0.404 | $2.0 \cdot 10^{-4}$ | $1.3 \cdot 10^{-3}$ | 4 | 22 | 42 |
| 7 | 2 | 0.404 | $2.0 \cdot 10^{-4}$ | $1.5 \cdot 10^{-4}$ | 4 | 17 | 29 |
| 8 | 2 | 0.404 | $4.0 \cdot 10^{-3}$ | $2.5 \cdot 10^{-3}$ | 4 | 10 | 39 |
| 9 | 2 | 0.95 | $3.3 \cdot 10^{-3}$ | $2.1 \cdot 10^{-3}$ | −2 | 30 | 10 |
| 10 | 2 | 0.404 | $2.0 \cdot 10^{-4}$ | $1.5 \cdot 10^{-4}$ | −2 | 30 | 3 |
| 11 | 2 | 0.404 | $1.3 \cdot 10^{-2\,[c]}$ | — | 40 | 18 | 45 |
| 12 | 3 | 0.28 | $6.6 \cdot 10^{-4}$ | $2.5 \cdot 10^{-4}$ | 0 | 19 | 55 |
| 13 | 3 | 0.74 | $1.0 \cdot 10^{-3}$ | $4.1 \cdot 10^{-4}$ | 0 | 16 | 87 |
| 14 | 3 | 0.87 | $1.0 \cdot 10^{-2}$ | $3.0 \cdot 10^{-3}$ | 0 | 3 | 42 |
| 15[d] | 3 | 0.78 | $1.5 \cdot 10^{-2}$ | $4.5 \cdot 10^{-3}$ | 4 | 18 | 100 |
| 16 | 4 | 0.822 | $2.0 \cdot 10^{-2}$ | $7.5 \cdot 10^{-2}$ | 0 | 48 | 92 |
| 17 | 4 | 0.25 | $3.0 \cdot 10^{-3}$ | $1.7 \cdot 10^{-3}$ | 4 | 24 | 28 |
| 18 | 4 | 0.5 | $6.8 \cdot 10^{-4}$ | $3.8 \cdot 10^{-4}$ | 4 | 24 | 29 |
| 19 | 5 | 0.15 | $1.8 \cdot 10^{-3\,[e]}$ | — | 45 | 23 | 8 |
| 20 | 5 | 0.24 | $1.0 \cdot 10^{-2}$ | $4.2 \cdot 10^{-3}$ | 4 | 23 | 26 |
| 21 | 5 | 0.3 | $9.0 \cdot 10^{-4\,[e]}$ | — | 35 | 46 | 10 |
| 22 | 5 | 0.72 | $1.2 \cdot 10^{-4}$ | $5.3 \cdot 10^{-3}$ | −1 | 46 | 2 |

[a] Conc. of (NH$_4$)$_2$S$_2$O$_8$; oxidative part of the redox couple.
[b] Conc. of Na$_2$S$_2$O$_5$; reductive part of the redox couple.
[c] Initiator: H$_2$O$_2$.

TABLE 5-continued

Details of the preparation or poly(vinylsaccharide)s by solution polymerization in water

| Sample No. | Monomer type | Monomer conc. in mol/l | Oxi. conc.[a] in mol/l | Red. conc.[b] in mol/l | Reaction temp. in °C. | Reaction time in h | Yield in % |
| --- | --- | --- | --- | --- | --- | --- | --- |

[d]Polymerization in $D_2O$ as solvent. The reaction was carried out in a $^{13}C$ NMR-tube. An insoluble gel resulted.
[e]Initiator: 2,2'dimethyl-2,2'-azodipropanamidine hydrochloride.

The poly(vinylsaccharides) contained in the conjugate according to the present invention are e.g. obtainable from a polymerization of monomeric vinylsaccharides such as allyl-, alkylallyl-, alkoxycarbonylallyl-, vinylether-, acrylamide- and methacrylamide-saccharides as homopolymerisates or copolymerisates with e.g. maleic acid-anhydride, in particular of acryl- and methacrylsaccharides as well as their derivatives. Therefore the poly(vinylsaccharide) of the invention preferably contains a polymethacrylate, polyacrylate, poly(α-alkylacrylate), or poly(α-alkylmethacrylate) chain in which alkyl in this case represents a linear alkyl residue with 1 to 4 C atoms. The procedure for such polymerizations is known to one skilled in the art and is e.g. described by J. Klein et al in the aforementioned documents. The poly(vinylsaccharide) preferably has a molecular weight of 1000 to 1,000,000 daltons, particularly preferably 400,000 to 500,000 daltons.

In the conjugate according to the present invention the carbohydrate or saccharide derivative is preferably linked to the vinyl skeleton via an ether, ester or amido group. In this case the ether bridges are usually inert to chemical and enzymatic attack.

In a preferred embodiment the conjugate according to the present invention contains a spacer of 1 to 6, preferably 3 to 5 and in particular 4 C atoms between the saccharide derivative and vinyl backbone.

The saccharides contained in the conjugate according to the present invention include the entire group of carbohydrates, i.e. not only monosaccharides but also disaccharides whereby mannose as well as sorbose and in particular lactose, glucose, maltose and galactose are, however, preferred. In a particular embodiment according to the present invention the saccharides are amino sugars and/or sugar lactones. However, open-ring saccharides such as sugar alcohols which are e.g. obtainable by reduction of saccharoses with $NaBH_4$ are also particularly preferred.

Particularly preferred saccharide derivatives are 1-amino-1-deoxysaccharides as well as N-($C_1$-$C_4$ alkyl)-acrylate-N'-1-deoxysaccharose ureas and the corresponding methacrylate derivatives which are derived therefrom. In this case the alkyl groups represent a spacer between the urea bond and the vinyl ester. In this connection those derivatives are in turn particularly preferred which contain a $C_2$-alkyl group such as e.g. N-ethyl-methacrylato-N'-1-deoxyglucitol urea, N-ethyl-methacrylato-N'-1-deoxymaltitol urea, N-ethyl-methyl-acrylato-N'-1-deoxycellobiitol urea as well as N-ethyl-methacrylato-N'-1-deoxylactitol urea.

Preferred proteins are hexokinase, glucose-6-phosphate dehydrogenase, cholesterol esterase, glucose oxidase, peroxidase, lactate dehydrogenase, glutamate dehydrogenase, creatine amidinohydrolase, creatine kinase, α-glucosidase, alkaline phosphatase, urokinase, cholesterol oxidase or sarcosine oxidase.

The protein conjugate according to the present invention preferably has a weight ratio of protein to poly(vinylsaccharide) of 1:1 to 1:20, particularly preferred is a weight ratio of 1:3 to 1:6.

The invention also concerns a process for the production of protein-saccharide conjugates. In this process a poly(vinylsaccharide), preferably in aqueous solution, is covalently linked according to the present invention to the protein in a known way. The chemical or enzymatic methods for linking proteins to saccharides, in particular to polysaccharides are known to one skilled in the art and are described e.g. in EP-A-0 222 380 (U.S. Pat. No. 4,931,392 ), EP-A-0 069 379 (U.S. Pat. No. 4,460,683), and in EP-A-0 201 805 (U.S. Pat. No. 4,950,609) as well as in R. D. Schmidt, Adv. Biochem. Eng. (1979) 12, 41–118 wherein the above references are hereby incorporated by reference. In this process the carbohydrate moiety of the poly(vinylsaccharide) is usually reacted with an activating agent such as e.g. trichlorotriazine (TCT), cyanogen bromide or 1-cyano-4-di-methyl-aminopyridinium tetrafluoroborate (CDAP-BF4), in which the ratio of activating agent to carbohydrate is preferably 1:5 to 1:10. The poly(vinylsaccharide) activated in this way then reacts in an aqueous medium with the protein to form a covalent bond. A summary of such immobilization methods is described e.g. in J. Marshall, American Chemical Society Symposium, Series 123, (1980) 125–140 and in J. Cohen and M. Wilchek, Appl. Biochem. Biotech. 9 (1984), 285–305 wherein the above references are hereby incorporated by reference.

For the production process according to the present invention a poly(acrylsaccharide), poly(methacrylsaccharide), poly(α-alkylacrylsaccharide) or poly(α-alkylmethacrylsaccharide) in which alkyl represents a linear residue with 1 to 4 C atoms is preferably used as the poly(vinylsaccharide).

A poly(vinylsaccharide) is preferably used in this process which is produced by reacting 1-aminomonosaccharides or/and -disaccharides with an isocyanate which has a polymerizable double bond and polymerization of the product obtained in this way.

In addition it is preferred in the process according to the present invention that a poly(vinylsaccharide) with a molecular weight of 1000 to 1,000,000 daltons be used.

In addition it is preferred for the conjugate formation that the protein poly(vinylsaccharide) are used in a ratio of 1:1 to 1:20, in particular 1:3 to 1:6 respectively.

The modified poly(vinylsaccharide) protein conjugates according to the present invention are also stable over a long period and are therefore particularly suitable for use in clinical chemical reagents. The invention thus also concerns their use in such reagents.

The invention is elucidated by the following examples in conjunction with the figures.

BRIEF DESCRIPTION OF THE DRAWINGS

FIG. 1 shows in this connection the temperature stability of an enzyme modified by a poly(vinylsaccharide) according to the present invention compared to an enzyme modified by dextran and the native enzyme;

FIG. 2 shows the turbidity properties of the conjugate according to the present invention in comparison with the enzyme modified by dextran and the native enzyme and FIG. 3 shows a comparison of the turbidity stabilities.

EXAMPLE 1

Synthesis of N-ethyl-methacrylato-N'-1-deoxyglucitol urea (1)

20 g 1-amino-1-deoxyglucitol (1a) are dissolved according to the method of Klein et al. (S. Engelke, Thesis, TU Braunschweig, FRG (1989)) in 100 ml water and cooled to −3° C. At this temperature 10 g isocyanatoethyl-methylacrylate (IEM, Dow Chemical) are added dropwise while stirring vigorously and during which the inner temperature is kept below 50° C. After completion of the isocyanate addition it is stirred for 12 hours and heated to room temperature. During the reaction time the emulsion which forms becomes a clear colourless solution. Subsequently the aqueous solution is extracted with ether in order to remove traces of undissolved isocyanate. After lyophilizing the solution the crude product is dissolved in methanol and recrystallized from acetone/ether (yield 35.3 g 95%); melting point 93° C. N-ethylmethacrylato-N'-1-deoxymaltitol urea (2), N-methylacrylato-N'-1-deoxycellobiitol urea (3) as well as N-ethylmethacrylato-N'-1-deoxylactitol urea (4) are produced in a corresponding manner from the corresponding 1-amino-1-deoxy sugars.

EXAMPLE 2

Poly(methacrylamidomaltose)/α-glucosidase conjugate 500 mg poly(methacrylamidomaltose) (PVS-maltose; produced according to Example 9, m.w. 500,000, Staudinger-Index in 0.1M $Na_2SO_4$=23 ml/g) are dissolved in 20 ml water and 200 mg 1-cyano-4-dimethylamino-pyridinium-tetrafluoroborate (CDAP) and 2.4 ml triethylamine (TEA) are added and adjusted to pH 8.4 with 1M $KH_2PO_4$. The activated PVS-maltose obtained in this way is combined with 5 ml α-glucosidase (Boehringer Mannheim) equivalent to 200 mg protein (dissolved in 10 mM potassium phosphate buffer, pH 7.8) and the pH is adjusted to a pH value of 7.6 with 1M $KH_2PO_4$. An opal solution is obtained in this process. After incubating for 4.5 hours at room temperature it is dialyzed overnight against 10 l of a 50 mM potassium phosphate buffer solution, pH 7.15. 27 ml of a PVS-maltose-glucosidase conjugate dialysate with 106 U/ml is obtained in this way.

A FPLC of 2 mg of the conjugate obtained in this way over Superose 6 (Pharmacia Uppsala Sweden) showed that 98% of the enzyme used is bound to the poly(vinylsaccharide) (conditions: pressure 20 bar, measurement at 280 nm, retention time of the native enzyme 39.6, conjugate 14.98).

EXAMPLE 3 (comparison)

Dextran-T40-α-glucosidase conjugate 2 g dextran-T40 with 20 ml water, 400 mg CDAP and 4.8 ml TEA are adjusted to pH 8.5 with a 1M $KH_2PO_4$ solution as described in Example 2. After completion of the activation 5 ml of the activated dextran solution are combined with 5 ml α-glucosidase. The solution remains clear at a pH of 7.6 (adjusted with $KH_2PO_4$). 10.5 ml of a dextran/glucose conjugate dialysate with 284 U/ml is obtained in this way.

Dextran T fractions are narrow, well-defined fractions obtained from native dextran produced by Leuconostoc mesenteroides. They consist of linear chains of α(1–6)-linked D-glucopyranosyl residues with occasional branches due to α(1–3)-linkages and cover the molecular weight range from 10,000 to 2,000,000. Dextran T fractions contain less than 5 ppm of heavy metals and are relatively resistant to hydrolysis.

The average weight molecular weight of Dextran T-40 is 40,000. The above definition is found in the 1989 Pharmacia LKB Biotechnology Products Catalogue.

EXAMPLE 4

A glutamate dehydrogenase-poly(vinylsaccharide) conjugate is produced as described in Example 3.

EXAMPLE 5

A glutamate dehydrogenase-dextran-T40 conjugate is produced as described in Example 3.

EXAMPLE 6

The temperature stability of the modified α-glucosidases produced in Examples 2 and 3 is determined. In this procedure conjugates with an activity of 20 U/ml are each stressed at a temperature of 45° C. in a 50 mM potassium phosphate buffer, pH 7.1 and the activity is determined every 15 minutes.

This procedure shows that the native enzyme is already completely inactivated after 60 minutes and that the enzyme modified by dextran has a residual activity of only about 20% after a two hour treatment whereas the polyvinylmaltose derivative still has a residual activity of at least 65% after a two hour treatment. Moreover, the enzyme modified by poly(vinylsaccharide) showed a constant residual activity after a 45 to 60 minute treatment or incubation which hardly decreased any further. The results are shown in FIG. 1.

In addition the turbidity of solutions of the native and the modified α-glucosidase was determined at an incubation temperature of 37° C. The results of this are shown in FIG. 2. These showed that the α-glucosidase modified according to the present invention still did not show any signs of turbidity even after a 12 hour incubation.

EXAMPLE 7

Turbidity of glutamate dehydrogenase

The turbidity stability of glutamate dehydrogenase is determined as described in Example 6. In this procedure 2 mg protein per ml are incubated at 30° C. in a 250 mM Tris buffer, pH 7.85. The results are shown in FIG. 3. This showed that the turbidity of the enzyme modified according to the present invention only increases by about 25% in a 64 hour incubation whereas the turbidity of the enzyme modified with dextran-T40 according to the state of the art increases in the same period by 175%.

EXAMPLE 8

1-methacrylamido-1-deoxymaltitol 100 g 1 amino-1-deoxymaltitol $\hat{=}$0.291 mol (m.w. 343.3)
44.86 g methacryl acid anhydride $\hat{=}$0.291 mol (m.w. 154.17)

150 ml dried methanol at −5° C. are placed in a 500 ml three-necked flask and 25 g (0.073 mol) 1-amino-1-deoxymaltitol (pulverized) are suspended in it. It is cooled to −10° C. and 11.26 g (0.073 mol) methacrylic acid-anhydride are added slowly dropwise. Afterwards it is heated to 0° C. and stirred at this temperature for 24 hours. Subsequently it is stirred for 90 h at +4° C. It is filtered at room temperature over a plaited filter and concentrated by evaporation at a bath temperature of 30° C. maximum. The yellow oil obtained in this way is taken up in 50 ml water and extracted 1× with 100 ml peroxide-free ether and 3× with 50 ml peroxide-free ether. The water is drawn off in a high vacuum at max. 30° C. and it is dried overnight in a desiccator over $P_2O_5$.

Initial weight: ca 40 g

It is dried further over $P_2O_5$ in the desiccator: 31.31 g=104% of the theoretical yield.

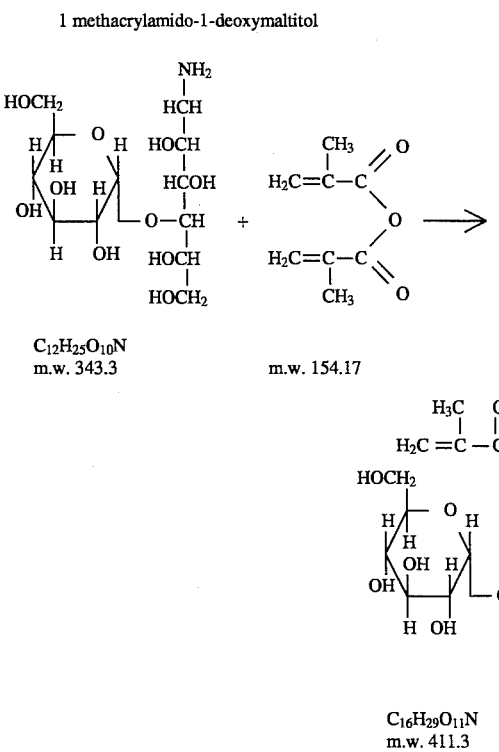

EXAMPLE 9

Polymerization of 1-methycrylamido-1-deoxymaltitol 20 g monomer (H 443)≙0.97 mol/l 91.2 mg $(NH_4)_2S_2O_8$≙8-10$^{-3}$ mol/l 46.3 mg $Na_2S_2O_5$≙4.0-10$^{-3}$ mol/l initiators Volume: 50 ml redistilled $H_2O$ Time: 4 days Temp: 4° C.

The monomer (produced according to Example 8) dissolved in 40 ml redistilled $H_2O$ is placed in a 250 ml three-necked flask with a $N_2$ balloon (nitrogen atmosphere), septum and stopper. It is cooled to 4° C. and the initiators are added. For this the salts are each dissolved in 5 ml redistilled $H_2O$ and first the ammonium peroxodisulphate and then the sodium disulphite are injected through the septum. After stirring for 4 days 3 l methanol containing 0.1% sodium acetate are added dropwise to the preparation. The white product which precipitates is filtered off under a vacuum. After a short drying it is dissolved in ca 50 ml redistilled $H_2O$ and precipitated again in 3 l methanol by dropwise addition.

Weight: 6.22 g poly(methacrylamidomaltose)

It will be understood that the specification and examples are illustrative but not limitative of the present invention and that other embodiments within the spirit and scope of the invention will suggest themselves to those skilled in the art.

We claim:

1. Water-soluble protein-saccharide conjugate wherein the protein is covalently bound to a poly(vinylsaccharide) via a saccharide residue.

2. The protein-saccharide conjugate of claim 1 wherein the saccharide residue is lactose, glucose, maltose or galactoside.

3. Protein-saccharide conjugate of claim 1 wherein the saccharide residue is an amino sugar, a sugar lactone or an open-ring sugar alcohol.

4. Protein-saccharide conjugate of claim 1 wherein the saccharide residue is 1N-1-deoxysaccharide.

5. Protein-saccharide conjugate of claim 1 wherein the protein is selected from the group consisting of hexokinase, glucose-6-phosphate dehydrogenase, cholesterol esterase, glucose oxidase, peroxidase, lactate dehydrogenase, glutamate dehydrogenase, creatine amidinohydrolase, creatine kinase, α-glucosidase, alkaline phosphatase, urokinase, cholesterol oxidase and sarcosine oxidase.

6. The protein-saccharide conjugate of claim 1 wherein the poly(vinylsaccharide) comprises saccharide groups covalently bonded to a polyvinyl backbone which is selected from at least one chain of the group consisting of polymethacrylate, polyacrylate, poly (α-alkylacrylate) and poly(α-alkyl methacrylate) wherein alkyl represents a linear $C_1$-$C_4$ alkyl residue.

7. The protein-saccharide conjugate of claim 1 wherein the weight ratio of protein to poly(vinylsaccharide) is 1:1 to 1:20.

8. The protein-saccharide conjugate as claimed in claim 7, wherein the weight ratio of protein to poly(vinylsaccharide) is 1:3 to 1:6.

9. The protein-saccharide conjugate of claim 1 wherein the poly (vinylsaccharide) has a molecular weight of 1,000 to 1,000,000 daltons.

10. Protein conjugate of claim 1 wherein the poly(vinylsaccharide) has a molecular weight of 400,000 to 500,000 daltons.

11. Process for the production of water-soluble polysaccharide protein conjugates comprising conjugating a poly(vinylsaccharide) and a protein with formation of a covalent bond between the protein and the saccharide moiety of the poly(vinylsaccharide) polymer wherein the saccharide residue is then covalently linked to a vinyl residue of the polyvinyl chain of the poly(vinylsaccharide) via an ether, ester or amido group via a coupling reagent.

12. Process as claimed in claim 11, wherein a poly(acryl-, poly(methacryl-, poly(α-alkylacryl-, poly(-α-alkyl-methacryl-saccharide) is used as poly(vinylsaccharide) in which alkyl represents a linear $C_1$-$C_4$ residue.

13. Process as claimed in claim 10, wherein 1-cyano-4-dimethyl-aminopyridine tetrafluoroborate, trichlorotriazine or cyanogen bromide is used as the coupling reagent for the conjugate formation.

14. Process as claimed in claim 11, wherein a poly(vinylsaccharide) with a molecular weight of 1000 to 1,000,000 daltons is used.

15. Process as claimed in any one of claims 11 to 14 wherein the protein to poly(vinylsaccharide) weight ratio is 1:1 to 1:20 for the conjugate formation.

16. Process as claimed in claim 15 wherein the protein to poly(vinylsaccharide) weight ratio is 1:3 to 1:6.

17. Process of any one of claims 11 to 14 comprising reacting 1-amino-mono- or disaccharides with an isocyanate having a polymerizable double bond, polymerizing the product obtained and using the polymerized product as the poly(vinylsaccharide).

18. The protein-saccharide conjugate of claim 1 wherein there are 1 to 6 carbon atoms between the saccharide residue and the poly(vinylsaccharide).

19. The protein-saccharide conjugate of claim 1 wherein there are 4 carbon atoms between the saccharide residue and the poly(vinylsaccharide).

20. The protein-saccharide conjugate of claim 1 wherein the saccharide residue is linked to the poly(vinylsaccharide) via an ether, ester or amido group.

21. The protein-saccharide conjugate of claim 1 wherein the saccharide residue is mannose or sorbose.

22. The protein-saccharide conjugate of claim 1 wherein the saccharide residue is N-($C_1$–$C_4$ alkyl)-acrylate-N'-1-deoxysaccharose ureas or the methacrylate derivative thereof.

23. The protein-saccharide conjugate of claim 22 wherein the alkyl group represents a spacer between a urea bond and a vinyl ester.

24. The protein-saccharide conjugate of claim 1 wherein the saccharide residue is selected from the group consisting of 1-methacrylamido-1-deoxymaltitol, N-ethyl-methacrylato-N'-1 deoxymaltitol urea, N-ethyl-methacrylato-N'-1-deoxyglucitol urea, N-ethyl-methyl-acrylato-N'-1-deoxycellobiitol urea and N-ethyl-methacrylato-N'-1-deoxylactitol urea.

25. A protein-saccharide complex selected from the group consisting of poly(methacrylamidomaltose)/α-glucosidase, Dextran-T-40-α-glucosidase, glutamate dehydrogenase-poly-(vinylsaccharide) and glutamate dehydrogenase-dextran-T40.

26. In a method for enzyme analysis the improvement consisting of conducting the analysis wherein the enzyme is present as the protein-saccharide of claim 1.

27. In a test kit for enzymatic analysis the improvement wherein the enzyme is present as the protein-saccharide conjugate of claim 1.

\* \* \* \* \*

UNITED STATES PATENT AND TRADEMARK OFFICE
CERTIFICATE OF CORRECTION

PATENT NO : 5,480,790
DATED : January 2, 1996
INVENTOR(S): Tischer et al.

It is certified that error appears in the above-identified patent and that said Letters Patent is hereby corrected as shown below:

In Claim 25, column 16, lines 9-10 of the Patent, delete "dextran-T40"

and insert -- Dextran-T-40 --.

Signed and Sealed this

Nineteenth Day of May, 1998

Attest:

Attesting Officer

BRUCE LEHMAN

Commissioner of Patents and Trademarks